United States Patent [19]
Yamamoto et al.

[11] 4,298,284
[45] Nov. 3, 1981

[54] METHOD AND APPARATUS FOR MEASURING MAGNETOOPTIC ANISOTROPY

[75] Inventors: Manabu Yamamoto, Odawara; Seiichi Murayama, Kokubunji; Masaru Ito, Kodaira; Kounosuke Oishi, Mito, all of Japan

[73] Assignee: Hitachi, Ltd., Tokyo, Japan

[21] Appl. No.: 969,268

[22] Filed: Dec. 14, 1978

[30] Foreign Application Priority Data

Dec. 14, 1977 [JP] Japan ............................ 52-166953[U]

[51] Int. Cl.³ ............................................ G01N 21/21
[52] U.S. Cl. .................................................. 356/368
[58] Field of Search ................................. 356/367, 368

[56] References Cited

U.S. PATENT DOCUMENTS 2,973,684  3/1961  Nisle ...................................... 356/368
4,035,083  7/1977  Woodriff et al. ...................... 356/368

OTHER PUBLICATIONS

Baily et al. "An Apparatus for Measurement of Electrically Induced Birefringence . . ." *Journal of Colloid and Interface Science*, vol. 45, No. 1 (Oct. 1973) pp. 177–189.
Dmitriev et al. "An Automatic Ellipsometer" *Instruments and Experimental Techniques*, vol. 16, No. 6, pt. 2 (Nov.–Dec. 1973; pub. May 1974)pp. 1792–1793.

*Primary Examiner*—Richard A. Rosenberger
*Attorney, Agent, or Firm*—Craig & Antonelli

[57] ABSTRACT

In measuring a change in the polarization state of light attributed to magnetooptic anisotropy, a means for generating optic anisotropy is added to a light source or onto an optical path extending from the light source to a polarization analyzer. This allows high precision analysis of the polarization state of light emergent from the polarization analyzer.

2 Claims, 8 Drawing Figures

METHOD AND APPARATUS FOR MEASURING MAGNETOOPTIC ANISOTROPY

FIELD OF THE INVENTION

This invention relates to a method and apparatus for measuring a minute change in the polarization state of light ascribable to magnetic anisotropy.

PRIOR ART OF THE INVENTION

There have been known in the prior art various photometric methods and apparatuses which measure changes in the polarization state of light ascribable to magnetooptic polarization rotation (Faraday effect) and magnetic birefringence (Voigt effect). For example, one known method is to irradiate a magnetized sample by linearly polarized light. Then the polarization component of light emergent from the sample which is orthogonal to the entering linearly-polarized light is measured with a polarization analyzer.

Figure 1:
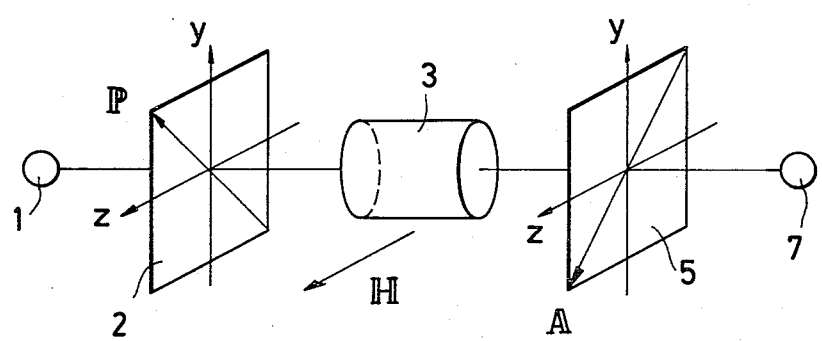
FIG. 1 is a constructional view of prior art apparatus for measuring a change in the polarization state of light attributed to magnetooptic anisotropy.

The principle of such a prior art method of measuring the change in the polarization state of the emergent light caused by the magnetooptic effect is illustrated in FIG. 1. Light radiated from a light source 1 is converted by a polarizer 2 into linearly polarized light having a polarization component in the direction of a vector P. This linearly polarized light then enters a sample 3. Light emerging from the sample 3 is received by a photodetector 7 through an analyzer 5 whose polarization plane is oriented to be orthogonal to that of the polarizer 2.

When a magnetic field H is applied to the sample 3, optic anisotropy is caused in the sample by the magnetooptic effect. This phenomenon is called magnetic birefringence. Light having passed through a magnetically birefringent substance exhibits a polarization state different from that of light entering the substance. This situation is shown in FIG. 2.

Figure 2:
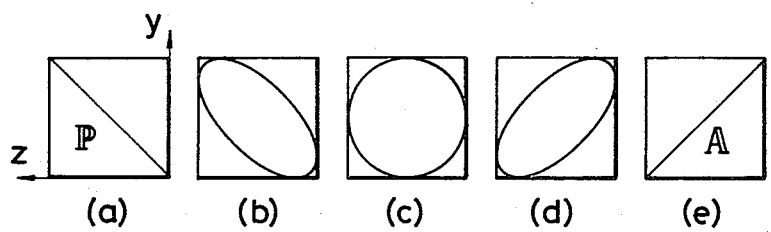
FIGS. 2 and 3 are diagrams for explaining the principles of measuring the polarization state of light attributed to magnetooptic anisotropy in the prior art and this invention.

In (a) of FIG. 2, the locus of the tip of the electric vector of entering light is observed in a direction parallel to the optical path and opposite to the traveling direction of the light beam. This locus agrees with the vector P which represents the polarization direction of the entrance polarizer 2. Light having passed through the sample 3 becomes elliptically polarized light as shown in (b) of FIG. 2 on account of the birefringence which the sample presents. As the birefringence of the sample 3 becomes more intense, the light having passed through the sample becomes closer to circularly polarized light as shown in (c) of FIG. 2. Further, it turns into elliptically polarized light as shown in (d) of the figure. Finally, it turns into linearly polarized light as shown in (e) of the figure. The polarization direction of this linearly polarized light agrees with a vector 1A which represents the orientation of the analyzer 5.

Figure 3:
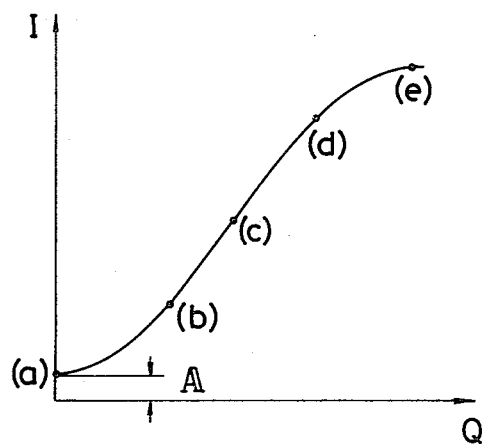

FIG. 3 illustrates how the intensity of the light passing through the analyzer 5 varies with the changes of the polarization state. The axis of abscissas represents the magnitude Q of the optic anisotropy exhibited by the sample 3. The magnitude Q is proportional to ($n_o - n_e$) where $n_o$ and $n_e$ denote the refractive indices of the sample for lights polarized in the Z-axial and Y-axial directions respectively. The axis of ordinates in FIG. 3 indicates the intensity of the light passing through the analyzer 5. Letters (a)-(e) in FIG. 3 correspond respectively to the polarized lights (a)-(e) in FIG. 2, and denote the respective light intensities obtained through the analyzer 5.

In the prior art, the entering light is linearly polarized light. Accordingly, in a case where the anisotropy of the sample is low, the operating point corresponds to the position (a) in FIG. 3. In this method, in a case where the atomic number density N of the sample in a unit volume is low, the light intensity I to be detected is expressed by:

$$I = A + B \cdot N^2 \qquad (1)$$

The constant A in this formula is a disturbance component which is attributed to stray light, leakage light, light emission of a furnace or flames for atomizing the sample, etc. The constant B is dependent upon the wavelength of light, the magnetooptic interaction length, the magnitude of magnetooptic anisotropy, etc. In the case of low densities N, the signal component given by the second term of the above equation becomes infinitesimal in the second order, and its detection is difficult on account of the disturbance by noise in the first term. It is also inconvenient for practical use since the relation between I and N becomes a quadratic equation. Further, Woodriff in U.S. Pat. No. 4,035,083 has disclosed a background corrected measurement of the concentration of a traced element which utilizes a magnetooptic effect which takes place when incident atomic resonance light is scattered by a sample subject to an externally applied transverse magnetic field. However, since said incident atomic resonance light is used only in a plain polarized state, when the anisotropy of the samplest low, the operating point corresponds to the position (a) in FIG. 3.

SUMMARY OF THE INVENTION

Accordingly, one object of the present invention is to provide a method and apparatus for measuring a minute change in the polarization state of light ascribable to magnetooptic anisotropy which eliminates the disadvantages of the prior art as described above.

To accomplish this and other objects in measuring the magnetooptic anisotropy of a sample according to the present invention, a means for generating optical anisotropy is added for a bias onto an optical path. That is, means for generating circularly polarized light or elliptically polarized light is added to the light source itself or onto an optical path extennding from the light source to a polarization analyzer. The means for generating circularly polarized light or elliptically polarized light is essentially different from the prior art method or apparatus for measuring a change in the polarization state of light attributed to magnetooptic anisotropy in that it is added anew as a bias to the magnetooptic anisotropy of a sample.

According to this invention, the intensity I of light permeating through the analyzer has a certain finite "leakage light", and simultaneously, with respect to the change of the polarization state corresponding to an anisotropic change caused in the sample by the application of a magnetic field, a light intensity proportional to the quantity of the change is added. As a result, the intensity of light entering a photodetector is expressed as follows for the intensity $I_0$ of light entering the sample:

$$I = I_o(C + D \cdot N)$$

Here, N is assumed to be low. Letter C is a constant dependent upon the ellipticity of the entering light and the orientation of the analyzer, while letter D is a constant dependent upon the wavelength of light, the magnetooptic interaction length, the intensity of the magnetic field, etc.

As apparent from the above equation, in the measuring method of this invention, the light intensity to be obtained becomes a linear function of the atomic number density N of the sample, which is advantageous over the prior art measuring method. A further advantage is that, since the light intensity to be obtained is high, even a very small change can be accurately measured.

Hereunder, embodiments of this invention will be described.

DESCRIPTION OF THE PREFERRED EMBODIMENTS

Embodiment 1

Figure 4:
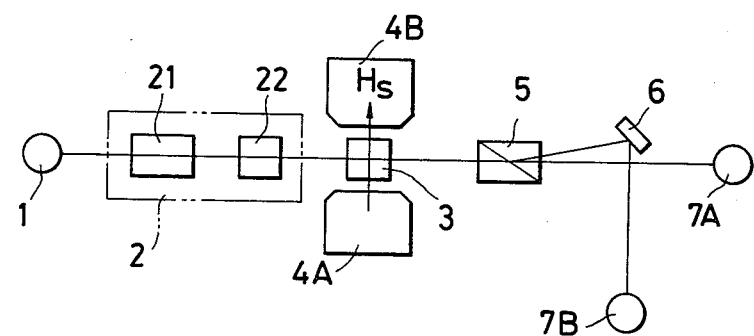
FIGS. 4, 5 and 6 are constructional views of apparatuses for measuring magnetooptic anisotropy according to this invention.

As illustrated in FIG. 4, light from a light source 1 (for example, an incandescent lamp, a discharge lamp, or a laser) is turned into elliptically or circularly polarized light or has its ellipticity changed through an elliptically or circularly polarized light-generator 2 and irradiates a sample 3. One known elliptically or circularly polarized light-generator for this purpose is a combination of a linear polarizer 21 and an optically anisotropic element (for example, a quarter-wave plate) 22. Although not shown in the figure, a wavelength selecting means such as filter and spectroscope is used as may be needed. A magnetic field $H_S$ orthogonal to an optical path is applied to the sample 3 by magnetic poles 4A and 4B. The direction and intensity of the magnetic field may be either fixed or variable.

With such a construction, light emergent from the sample 3 is separated by a birefringent analyzer 5 into two polarization components which are orthogonal to each other. The respective polarization components are measured by photodetectors 7A and 7B. The analyzer 5 need not be birefringent, but may be an element which takes out only one polarization component. In the apparatus described above, a reflector 6 may be used if necessary in the arrangement of the optical system.

In the above embodiment, the arrangement of the elliptically or circularly polarized light-generator 2 between the light source 1 and the sample 3 signifies that the operating point (a) in FIG. 3 at the time when the elliptic or circular polarization generator is not interposed is moved to the operating points (b), (c), (d), etc. That is, in measuring a minute anisotropy which is caused by the sample 3, the means for generating further anisotropy is added onto the optical path, thereby to bestow a certain finite bias on the magnitude of the optic anisotropy over the full length of the optical path. Thus, as is apparent from FIG. 3, the transmitted light 1 through the analyzer 5 comes to have leakage light of a certain finite value. Simultaneously, for the minute change of the anisotropy Q, a variation of the intensity I proportional thereto is caused.

Theoretical analyses and experimental results have revealed that, letting $I_o$ denote the intensity of the light entering the sample 3, the intensities of the light beams entering the photodetectors 7A and 7B are generally represented as follows, respectively:

$$I_A = I_o(C_a + D_a \cdot N) \quad (2)$$

$$I_B = I_o(C_b + D_b \cdot N) \quad (3)$$

Here, the atomic number density N is assumed to be low. As understood from the equations, $I_A$ and $I_B$ become linear functions of N in the system of this invention. Besides, the absolute value of the term $D_j \cdot N (j=a, b)$ indicative of the output signal is greater than the signal output (quadratic with respect to N and infinitesimal) of the prior art system. This leads to the advantage that the apparatus is less susceptible to any disturbance due to the light emission of the furnace.

With the method explained above, by measuring the light intensity $I_A$ or $I_B$ the atomic number density N can be evaluated from the relation of Eq. (2) or Eq. (3).

In Eqs. (2) and (3), $C_a$ and $C_b$ are constants which depend upon the ellipticity of the entering elliptically or circularly polarized light and the orientation of the analyzer. $D_a$ and $D_b$ are constants which depend upon the light wavelength, the magnetooptic interaction length, the intensity of the magnetic field, etc. In a special case where the entering light is circularly polarized light and where the orientation of the analyzer 5 is 45° to the magnetic field $H_s$, the following relations hold:

$$C_a = C_b = C \,(C \text{ is a constant}) \quad (4)$$

$$D_J = -\gamma - [\alpha\theta]q \quad (5)$$

Here, $[\alpha\theta]$ represents the sign of the product $\alpha\theta$. $\alpha$ denotes a quantity whose sign is inverted in dependence on the polarization state in such a manner that it is plus when the additional circular or elliptic polarization generating means is means for generating counterclockwise circularly or elliptically polarized light and that it is minus when the additional means is means for generating clockwise circularly or elliptically polarized light. $\theta$ denotes an angle which represents the polarization direction of light to be selected by the analyzer 5, with reference to the direction of the magnetic field $H_s$ (that is, $\theta = \pm \pi/4$ in the present embodiment). q and $\delta$ denote the intensities of birefringence and absorption of the sample per unit atomic number density. Under the conditions where $\theta = +\pi/4$ corresponds to the photodetector A and $\theta = -\pi/4$ corresponds to the photodetector B, Eqs. (4) and (5) are substituted into Eqs. (2) and (3). Then, $$I_A = I_o\{C - \gamma N - [\alpha]qN\} \quad (6)$$

$$I_B = I_o\{C - \gamma N + [\alpha]qN\} \quad (7)$$

Accordingly, there are obtained:

$$I_A - I_B = -[\alpha] \cdot 2I_o q N \qquad (8)$$

$$I_A + I_B = 2I_o\{C - \gamma N\} \qquad (9)$$

and $$(I_A - I_B)/I_o = -[\alpha] \cdot 2qN \qquad (10)$$

$$(I_A - I_B)/(I_A + I_B) = -[\alpha]qN/\{C - \gamma N\} \qquad (11)$$

With the principle expressed by Eqs. (6) to (11), improved measuring methods as below stated can be realized:

(1) When the difference between the output $I_A$ of the photodetector 7A and the output $I_B$ of the photodetector 7B is taken, it is proportional to the atomic number density N, and the fixed bias component is eliminated. (In order to obtain the difference between $I_A$ and $I_B$, a conventional operational amplifier is used.)

(2) When $(I_A - I_B)$ is divided by the entering light intensity $I_o$ or $(I_A + I_B)$, a signal output dependent upon the atomic number density is obtained irrespective of $I_o$. A technique for such division is well known.

When the analyzer 5 is rotated about the optical path, signals corresponding to $I_A$ and $I_B$ can be derived successively in time by the use of either the photodetector 7A or 7B.

Although FIG. 4 shows the linear polarizer 21 and the optically anisotropic element 22 as being between the light source 1 and the sample 3, it should be understood that this can be rearranged so that the linear polarizer 21 is between the light source and the sample while the optically anisotropic element 22 is between the sample and the birefringent analyzer 5.

Embodiment 2

Figure 5:
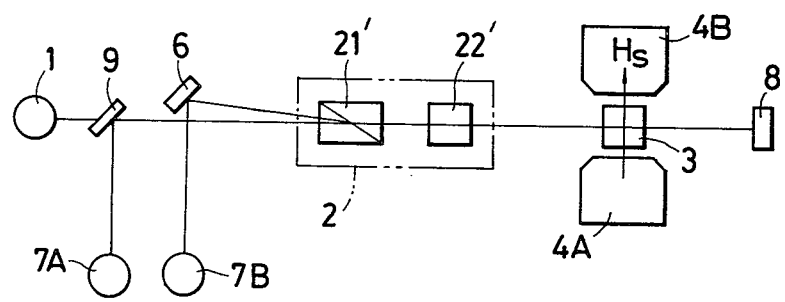

In an embodiment shown in FIG. 5, light radiated from a light source 1 is converted into elliptically or circularly polarized light by an elliptically or circularly polarized light-generator 2, and the elliptic or circular polarization light irradiates a sample 3 to which a magnetic field is applied orthogonally to an optical path. Light emergent from the sample 3 is caused to retrograde on the entering optical path by a reflector 8. It is passed through the sample 3 again, and has its ellipticity changed by the elliptic or circular polarization generator 2. Herein, it is separated into two polarization components orthogonal to each other by means of a birefringent polarizer 21'. The two polarization components are respectively reflected by reflectors 6 and 9 and detected by photodetectors 7B and 7A.

The embodiment illustrated in FIG. 5 has the reflector 8 added onto the optical path, and thereby brings forth the following advantages:

(1) Since the light passes through the sample 3 twice, the magnetooptic interaction length is extended, and the detection sensitivity is improved.

(2) In case of exploiting an optoelastic effect or an electrooptic effect for an optically anisotropic element 22, a mechanical force or a voltage which is externally applied can be reduced by half.

In FIG. 5, the semitransparent mirror 9 serves to conduct the light emergent from the sample 3 to the photodetector 7A.

In the foregoing embodiment of FIG. 4, when the anisotropic element 22 is the quarter-wave plate, the light incident on the sample becomes circularly polarized light. In order to operate the apparatus of FIG. 5 under the same condition, the anisotropic element 22' must be a ⅛-wave plate.

More specifically, the light entering the sample 3 is elliptically polarized light whose orthogonal components have a phase difference of $\pi/4$. However, the light reflected from the reflector 8 turns into circularly polarized light after having passed through the anisotropic element 22' again.

Further, even when the optically anisotropic element 22 is arranged between the sample 3 and the analyzer 5 in the apparatus of FIG. 4, Eqs. (2) and (3) hold. In this case, the light incident on the sample 3 is linearly polarized light, and the light incident on the analyzer 5 is circularly polarized light or elliptically polarized light.

As thus far described, this invention is characterized in that the light by which the sample is irradiated may be any of linearly polarized light, elliptically polarized light and circularly polarized light, and that if the light is the linearly polarized light, it is converted into circularly polarized light or elliptically polarized light by the additional means in the optical path before it enters the analyzer.

Embodiment 3

Figure 6:
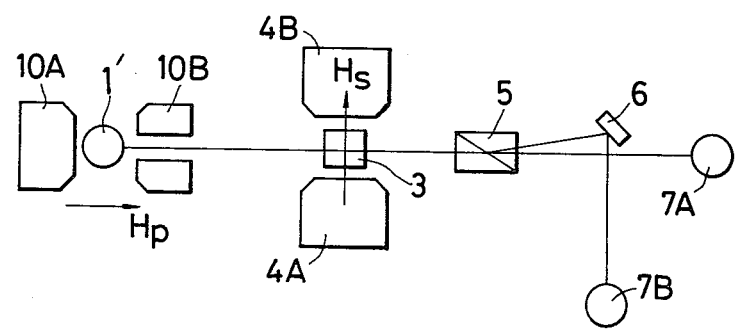

An embodiment shown in FIG. 6 fundametally has the same arrangement as that of the apparatus of Embodiment 1 (the arrangement of the apparatus in FIG. 4), but is further characterized by applying the Zeeman effect for the additional means for generating circularly polarized light. More specifically, a magnetic field $H_p$ is applied by magnetic poles 10A and 10B to an atomic resonance line source 1' in parallel with the optical path. The intensities of circularly polarized light components whose Zeeman shifts of frequencies are +p and −p are equal, and they are denoted by $I_o/2$. Further, $\alpha$ and q for the ±p components are respectively denoted by $\alpha(\pm p)$ and $q(\pm p)$. Then, Eqs. (6) and (7) become:

$$I_A = (I_o/2)\{C - \gamma N - [\alpha(+p)]q(+p)N\} + (I_o/2)\{C - \gamma N - [\alpha(-p)]q(-p)N\} \qquad (12)$$

Herein, since the +p component and the −p component are the circular polarizations of reverse courses to each other, $\alpha(+p)$ and $\alpha(-p)$ are opposite in sign. Owing to the nature of the refractive index dispersion in the vicinity of an atomic resonance line, q(+p) and q(−p) are opposite in sign and equal in absolute value. Accordingly, Eq. (12) becomes:

$$I_A = I_o\{C - \gamma N - [\alpha(+p)]q(+p)N\} \qquad (13)$$

Likewise, with respect to the photodetector 7B, $$I_B = I_o\{C - \gamma N + [\alpha(+p)]q(+p)N\} \qquad (14)$$

Eqs. (6) to (11) and the description associated therewith are applicable as they were described earlier.

As in the embodiment of FIG. 4, accordingly, the atomic number density N of the sample can be evaluated by measuring $I_A$ and $I_B$ either separately, simultaneously, or alternately. The intensity of the magnetic field $H_p$ which is applied to the light source 1' may be either fixed or variable. In case where the magnetic filed $H_p$ is an alternating field, a.c. outputs are obtained as $I_A$ and $I_B$, and this is effective for the detection of feeble signal components. The reason is that when the magnetic field $H_p$ is modulated by a frequency f, q is modulated by the frequency f, so components of the frequency f contained in $I_A$ and $I_B$ become signal components in the main.

In the apparatus of FIG. 6, a high-frequency lamp of 20 megahertz (MHz) and 100 watts (W) radiating an atomic resonance line of CdI, 228.8 nm was used as the light source 1', and a magnetic field $H_p$ of 0.21 tesla (T) was applied to the high-frequency lamp in parallel with the optical path by the magnetic poles 10A and 10B. A magnetic field $H_s$ of 1 tesla (T) was applied to the sample 3 orthogonally to the optical path by the magnetic poles 4A and 4B. Light emergent from the sample was separated through the analyzer 5 into two orthogonal polarization components, and the respective components were detected by the photodetectors 7A and 7B.

Figure 7:
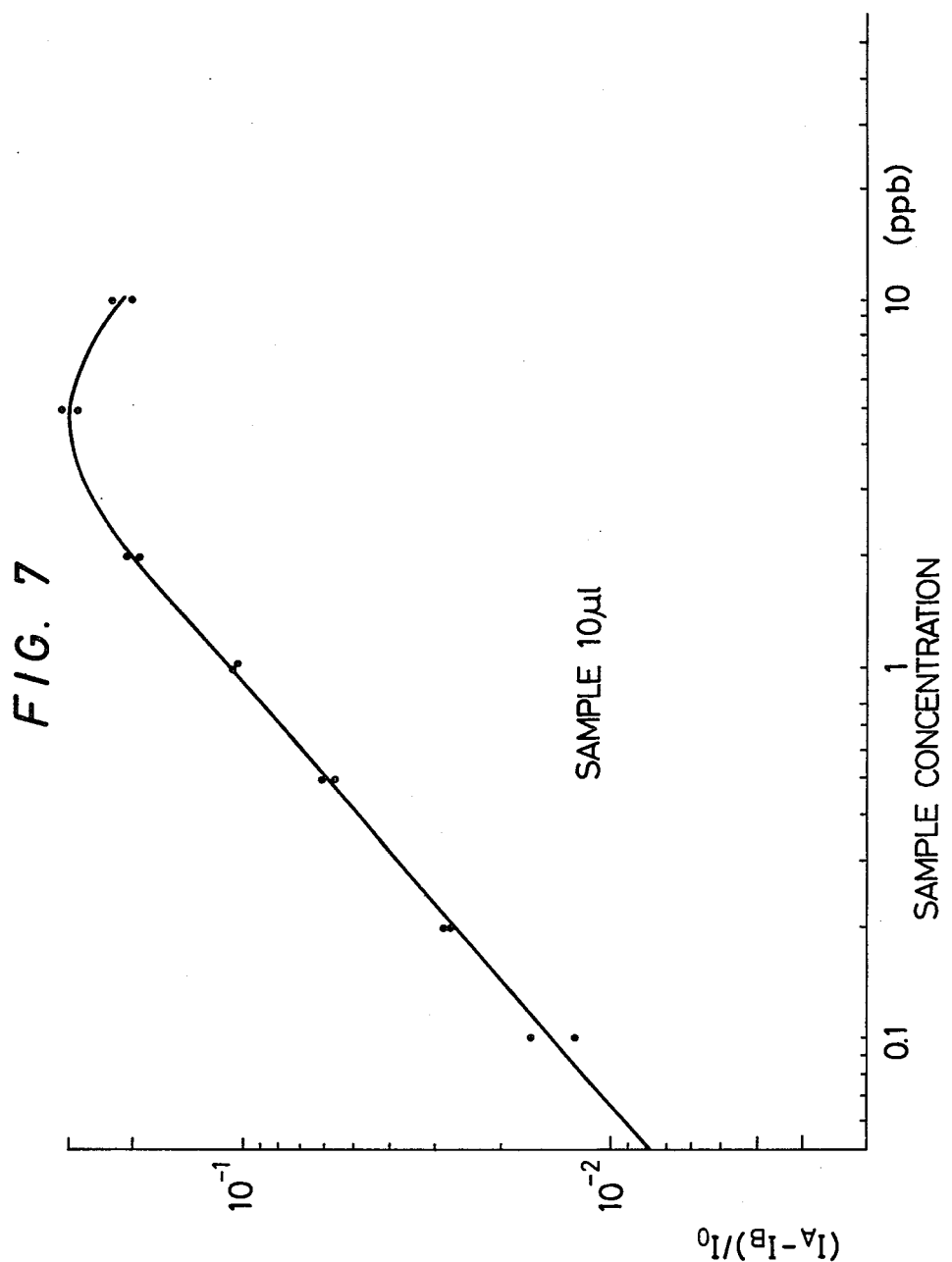
FIG. 7 is a characteristic diagram of sample amounts versus output signals measured by the apparatus of FIG. 6.
Figure 8:
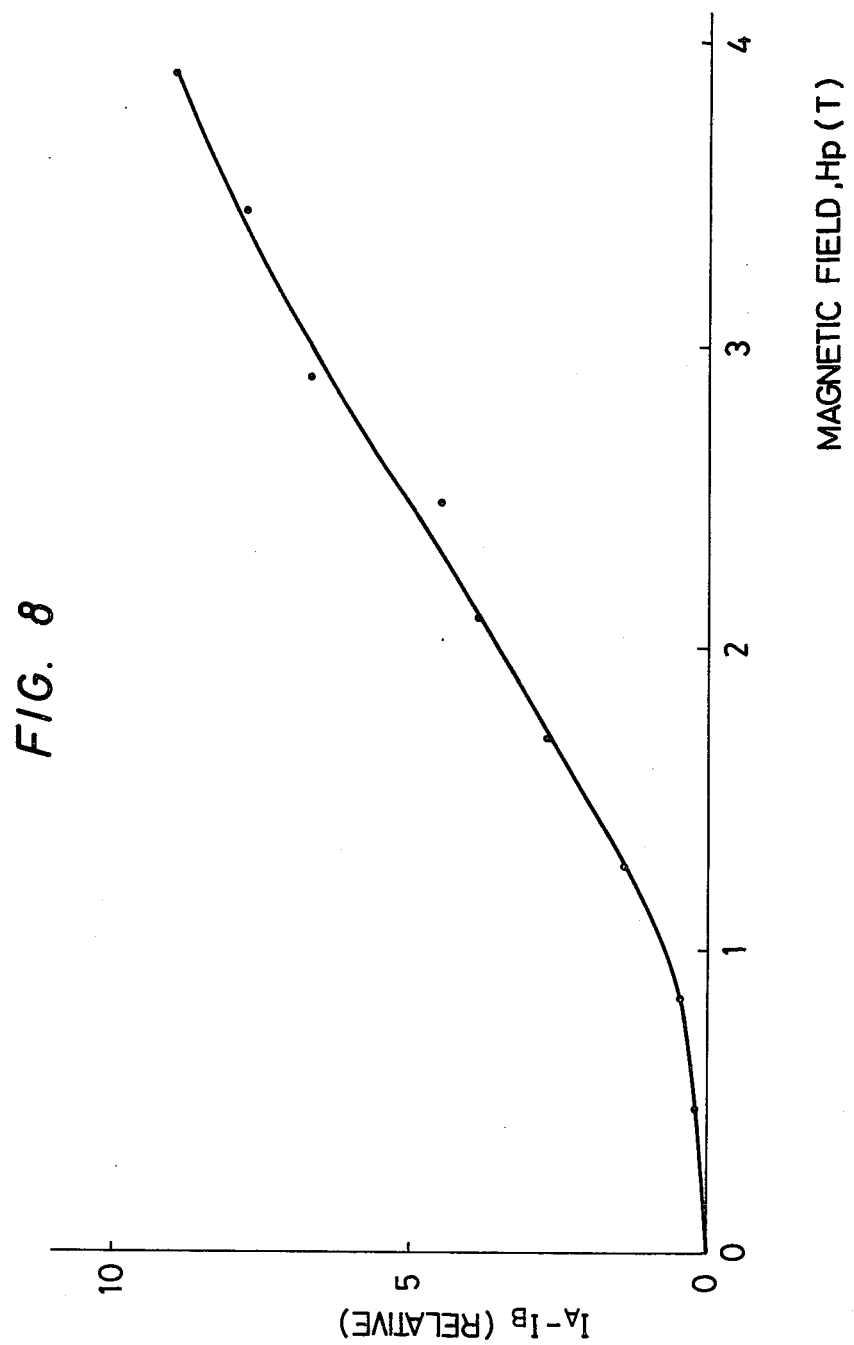
FIG. 8 is a characteristic diagram showing the relationship between magnetic fields and output signals at the time when the magnetic-field intensity was varied in the apparatus of FIG. 6.

A characteristic diagram of the sample concentration (in ppb) versus the light output in this case is shown in FIG. 7. As apparent from FIG. 7, the relationship between the sample concentration and the output becomes a linear proportional relation as in the case of the atomic light absorption. This signifies that the processing is simplified. Further, when the magnetic field applied to the light source was intensified, for example, to $H_p \approx 0.4$ T, the sensitivity was more enhanced as shown in FIG. 8.

While we have shown and described several embodiments in accordance with the present invention, it is understood that the same is not limited thereto but is susceptible of numerous changes and modifications as known to those skilled in the art and we therefore do not wish to be limited to the details shown and described herein but intend to cover all such changes and modifications as are encompassed by the scope of the appended claims.

We claim:
1. A apparatus for providing a measure of the concentration of a sample element by magnetooptic effect comprising:
   means for providing a sample element on an optical path, said element having a given atomic resonance frequency,
   means for subjecting said sample to a magnetic field transverse to said optical path,
   means for supplying and directing at said sample and along said optical path a beam of light,
   a polarizer on said optical path positioned to interrupt the emergent beam from said sample, and
   means to detect said emergent beam after passing through said polarizer, the improvement in said beam supplying means comprising;
   a light source radiating elliptically or circularly polarized light at a frequency shifted from the atomic resonance frequency of said element.

2. A method of providing a measure of the concentration of a sample element utilizing magnetooptic effect comprising the steps of;
   positioning a sample containing said element having a given atomic resonance frequency on an optical path,
   subjecting said sample to a magnetic field transverse to said optical path,
   directing along said optical path and at the sample a beam of light emitted by a light source radiating elliptically or circularly polarized light at a frequency shifted from the atomic resonance frequency of said element,
   passing said beam through a polarizer after emergence from said sample, and
   detecting the intensities of said emergent beam after it passes through said polarizer.

* * * * *